(12) United States Patent
Tatch (10) Patent No.: US 11,707,498 B2
(45) Date of Patent: Jul. 25, 2023

(54) METHOD OF USING A GEL, RINSE, AND SPRAY FOR MANAGEMENT OF POST-ORAL SURGICAL RECOVERY AND MAINTENANCE OF ORAL HEALTH

(71) Applicant: StellaLife, Inc., Northbrook, IL (US)

(72) Inventor: Walter Tatch, Northbrook, IL (US)

(73) Assignee: STELLALIFE, INC., Aventura, FL (US)

( * ) Notice: Subject to any disclaimer, the term of this patent is extended or adjusted under 35 U.S.C. 154(b) by 44 days.

(21) Appl. No.: 16/212,935

(22) Filed: Dec. 7, 2018

(65) Prior Publication Data
US 2019/0105364 A1 Apr. 11, 2019

Related U.S. Application Data

(63) Continuation of application No. 15/093,786, filed on Apr. 8, 2016, now abandoned.

(51) Int. Cl.
*A61K 36/714* (2006.01)
*A61K 36/28* (2006.01)
*A61K 36/75* (2006.01)
*A61K 36/56* (2006.01)
*A61K 41/00* (2020.01)
*A61K 45/06* (2006.01)
*A61K 36/68* (2006.01)
*A61K 35/618* (2015.01)
*A61K 33/28* (2006.01)

(52) U.S. Cl.
CPC ............ *A61K 36/714* (2013.01); *A61K 33/28* (2013.01); *A61K 35/618* (2013.01); *A61K 36/28* (2013.01); *A61K 36/56* (2013.01); *A61K 36/68* (2013.01); *A61K 36/75* (2013.01); *A61K 41/0004* (2013.01); *A61K 45/06* (2013.01)

(58) Field of Classification Search
CPC ...... A61K 36/48; A61K 36/82; A61K 36/714; A61K 33/28; A61K 35/618; A61K 36/28; A61K 36/56; A61K 36/68; A61K 36/75; A61K 41/0004; A61K 45/06; A61K 9/006; A61K 36/00; A61P 1/02
See application file for complete search history.

(56) References Cited

U.S. PATENT DOCUMENTS

| | | | |
|---|---|---|---|
| 5,376,374 A | 12/1994 | Zelaya | |
| 7,083,779 B2 | 8/2006 | Behl et al. | |
| 8,999,401 B2* | 4/2015 | Luria | A61Q 1/06 424/59 |
| 9,545,429 B1 | 1/2017 | Kaline | |
| 2003/0003140 A1 | 1/2003 | Domb et al. | |
| 2006/0280778 A1 | 12/2006 | Wilson | |
| 2007/0184128 A1 | 8/2007 | Dreyer | |
| 2008/0166435 A1 | 7/2008 | Pylypchuk | |
| 2008/0279902 A1* | 11/2008 | Luria | A61Q 19/005 424/59 |
| 2009/0087501 A1 | 4/2009 | Cummins | |
| 2009/0214711 A1* | 8/2009 | Bayani | A61K 31/417 426/66 |
| 2010/0303935 A1 | 12/2010 | Squires | |
| 2010/0316737 A1 | 12/2010 | Farrington et al. | |
| 2011/0038949 A1* | 2/2011 | Oswal | A61P 9/10 424/602 |
| 2011/0129552 A1 | 6/2011 | Saha et al. | |
| 2015/0283189 A1 | 10/2015 | Smit | |
| 2017/0290873 A1 | 10/2017 | Tatch | |
| 2021/0386811 A1* | 12/2021 | Tatch | A61K 36/45 |

FOREIGN PATENT DOCUMENTS

| | | | |
|---|---|---|---|
| GB | 1314136 | 4/1973 | |
| WO | 2009047005 A2 | 4/2009 | |
| WO | 2009047005 A3 | 4/2009 | |
| WO | WO-2009047005 A2 * | 4/2009 | ............ A61K 45/06 |

OTHER PUBLICATIONS

Boericke, W. Homœopathic Materia Medica. Internet posting date: 1999. Retrieved from the internet on: Oct. 24, 2020. Retrieved from: <URL: http://homeoint.org/books/boericmm/i/ign.htm>. (Year: 1999).*
Swanson. Swanson Health Products:Ignatia Amara 30X. Internet Archive Date: Nov. 5, 2012. Retrieved from the Internet on: 2021-0-18. Retrieved from: <URL: https://www.swansonvitamins.com/hylands-ignatia-amara-30x-250-tabs>. 1 page. (Year: 2012).*
Cheng, H. "Pharmasave: Cloverdale and Steveston Village". Web Publication date: Jul. 1, 2011. Retrieved from the Internet on: 2021-0-18. Retrieved from: <URL: https://ipharmasave.com/news/q-i-heard-that-echinacea-angustifolia-can-be-used-as-a-sedative-is-that-really-true/>. 2 pages. (Year: 2011).*
"Stress and Anxiety". Web Publication date: Jul. 1, 2011. Retrieved from the Internet on: 2021-0-18. Retrieved from: <URL: https://ipharmasave.com/news/q-i-heard-that-echinacea-angustifolia-can-be-used-as-a-sedative-is-that-really-true/>. 3 pages. (Year: 2011).*
(U1) Feder, L. Top Ten Homeopathic Remedies From Dr.Lauren Feder. Internet Posting Date: Mar. 31, 2012. Retrieved from the Internet on: 2021-0-18. Retrieved from: <URL: https://www.swansonvitamins.com/hylands-ignatia-amara-30x-250-tabs>. 13 pages. (Year: 2012).*
Extended European Search Report for corresponding European Application No. 17779517.6 entitled "Method of Using Homeopathic Kit Containing Gel, Rinse and Spray for Management of Post-Oral Surgical Recovery and Maintenance of Oral Health" dated Mar. 27, 2020.
Hoseinishad et al. "Homeopathy in Dentistry: A review", International Journal of Contemporary Dental and Medical Reviews, Jan. 1, 2015.

(Continued)

*Primary Examiner* — Aaron J Kosar
(74) *Attorney, Agent, or Firm* — Elmore Patent Law Group, PC; Carolyn S. Elmore (57) ABSTRACT

Homeopathic spray, gel, and rinse compositions containing tinctures of *Arnica montana, Calendula officinalis, Chamomilla, Ignatia amara, Echinacea purpurea* and/or *Echinacea angustifolia* are disclosed, along with homeopathic compositions containing tinctures of *Calendula officinalis, Echinacea purpurea, Plantago major,* and *Azadirachta indica*. Methods of using, and kits containing, the homeopathic spray, gel, rinse and other compositions for maintaining oral care and reducing inflammation, pain, and bruising after oral surgery are provided.

17 Claims, 2 Drawing Sheets

(56) References Cited

OTHER PUBLICATIONS

Lokken et al. "Effect of homoeopathy on pain and other events after acute trauma: Placebo controlled trial with bilateral oral surgery", British Medical Journal, vol. 310, No. 6992, 1995, pp. 1439-1442.
Singer et al. "Efficacy of a homeopathic preparation in control of post-operative pain—A pilot clinical trial", Acute Pain, Elsevier, vol. 9, No. 1, Mar. 19, 2007.
Yarom et al. "Systematic review of natural agents for the management of oral mucositis in cancer patients", Supportive Support Care Cancer, Springer, vol. 21, No. 11, Jun. 14, 2013, pp. 3209-3221.
Halberstein, R. A. "Botanical Medicines for Oral Health", Natural Product Communications, 2008, vol. 3, No. 11, pp. 1813-1824.
Goetz, P. "Phyto-aromatherapie de la conjonctivite" Phytotherapie, Springer-Verlag, Paris, FR, vol. 14, No. 1, Jan. 27, 2016 (Jan. 27, 2016), pp. 58-61.
International Search Report and Written Opinion for corresponding PCT Application No. PCT/US2017/023804 entitled "Method of Using Homeopathic Kit Containing Gel, Rinse and Spray for Management of Post-Oral Surgical Recovery and Maintenance of Oral Health" dated Jun. 21, 2017.
Partial Supplementary European Search Report for corresponding European Application No. 17779517.6 entitled "Method of Using Homeopathic Kit Containing Gel, Rinse and Spray for Management of Post-Oral Surgical Recovery and Maintenance of Oral Health" dated Dec. 18, 2019.
Petersen. The World Oral Health Report 2003 WHO/NMH/NPH/ORH/03.2.
Pozzi et al. Pain management for dentists: the role of ibuprofen. Ann Stomatol {Roma). Jul.-Dec. 2011; 2(3-4 Suppl): 3-24.
Osunde et al. Management of inflammatory complications in third molar surgery: A review of the literature. AfrHealth Sci. Sep. 2011; 11 (3): 530-537.
Hobdell. Global goals for oral health 2020. International Dental Journal (2003) 53, 285-288.
White ,RP Jr, Shugars , DA el.al. Recovery after third molar surgery; Clinical and health-related quality of life outcomes. J OMS, 2003; Issue 5,pp. 535-544.
Goldstein et al. Unconventional Dentistry: Part IV. Unconventional Dental Practices and Products. J Can Dent Assoc 2000; 66:564-8.
Goldberg et al. "Complications after mandibular third molar surgery: a statistical analysis of 500 consecutive procedures in private practice" J Am Dent Assoc., vol. 111, Aug. 1985, 277.
Osborn et al. "Prospective Study of Complications Related to Mandibular Third Molar Surgery" LJ Oral Maxillofac Surg. 43.767-769, 1985.
Hirschmann, JV. "Some principles of systemic glucocorticoid therapy" Clinical and Experimental Dermatology (1986) II, 27-33.
Seymour et al. "Pain control after third molar surgery" Int. J. Oral Surg. 1984; 13: 457-485.
Bystedt et al. "Effect of methylprednisolone on complications after removal of impacted mandibular third molars" Swed Dent J 1985; 9(2):65-9 [abstract].
Edilby et al. "A Double-blind Placebo-controlled trial of the effects of Daxamethansone on Postoperative Swelling" J Dent Res 61:556, 1982.
Seeley et.al "Effect of Homeopathic Arnica montanaon Bruising in Face-lifts; Results of a Randomized, Double-blind, Placebo-Controlled Clinical Trial" Arch Facial Plast Surg/ vol. 8, Jan./Feb. 2006.
Kaziro et al. "Metronidazole (Flagyl) and Arnica Montana in the Prevention of Post-Surgical Complications, a Comparative Placebo Controlled Clinical Trial" British Journal of Oral and Maxillofacial Surgery (1984) 22, 42-49.
Nayyar, et al. "Bupivacaine as pre-emptive analgesia in third molar surgery: Randomised controlled trial" British Journal of Oral and Maxillofacial Surgery 44 (2006) 501-503.
Shugars et.al. "Developing a Measure of Patient Perceptions of Short-Term Outcomes of Third Molar Surgery" J Oral Maxillofacial Surg 54:1402-1408, 1996.
Grossi et.al. "Effect of Submucosal Injection of Dexamethasone on Postoperative Discomfort After Third Molar Surgery: A Prospective Study" J Oral Maxillofacial Surg 2007, 65: 2218-2226.
Miles et al. "Reduction of Postoperative Facial Swelling by Low-Dose Methylprednisolone: An Experimental Study" J Oral Maxillofac Surg 51: 987, 1993.
Dampc et al. "Rhododendron Tomentosum (Ledum palustre). A review of Traditional Use Based on Current Research", Fitoterapia, vol. 85, Jan. 23, 2013.
International Search Report and Written Opinion for corresponding PCT Application No. PCT/US2019/054607 entitled "Compositions and Methods for Promoting and Maintaining Oral Health" dated Jan. 15, 2020.
Oberbaum et al. "Wound Healing by Homoeopathic Silicea Dilutions in Mice" British Homoeopathic Journal, vol. 82, No. 1, Jan. 1, 1993, pp. 61-67.
Silje Storehagen, Nanna Ose og Shilpi Midha. "Dentifrices and Mouthwashes Ingredients and Their Use", (Year: 2003).
Bouloux, G. et al., "Bupivicaine Versus Lidocaine for Third Molar Surgery: A Double-Blind, Randomized, Crossover Study", J. Oral Maxillofac. Surg., 57, 1999, 510.
Chen, et al., "Positional differences in the wound transcriptome of skin and oral mucosa", BMC Genomics, 11, doi:10.1186/1471-2164-11-471, 2010, 471.
Dionne, R. et al., "Dexamethasone Suppresses Peripheral Prostanoid Levels Without Analgesia in a Clinical Model of Acute Inflammation", J. Oral Maxillofac. Surg., vol. 61, 2003, 997.
Esen, E. et al., "Determination of Anti-Inflammatory Effects of Methylprednisalone on the Sequelae of Third Molar Surgery", J. Oral Maxillofac. Surg., 57, 1999, 1201.
Hargreaves, K. et al., "Dexamethasone Alters Plasma Levels of Beta-Endorphis and Postoperative Pain", Clin. Pharmacol. Ther., vol. 42, 1987, 601.
Kim, J. et al., "Minor Complications After Mandibular Third Molar Surgery: Type, Incidence, and Possible Prevention", OOO, 102, 2006, e4.
Noroozi, A-R et al., "Modern concepts in understanding and management of the "dry socket" syndrome: comprehensive review of the literature", Oral Surgery, Oral Medicine, Oral Pathology, Oral Radiology, and Endodontology, 107(1), https://doi.org/10.1016/j.tripleo.2008.05.043, Jan. 2009, 30-35.

* cited by examiner

METHOD OF USING A GEL, RINSE, AND SPRAY FOR MANAGEMENT OF POST-ORAL SURGICAL RECOVERY AND MAINTENANCE OF ORAL HEALTH

CROSS REFERENCE TO RELATED APPLICATIONS

This application is a continuation application of U.S. Ser. No. 15/093,786 filed Apr. 8, 2016.

FIELD OF THE INVENTION

The present invention relates generally to compositions and methods for oral health and maintenance. Specifically, the present invention relates to the general maintenance of a healthy oral cavity, general dental care and methods of decreasing pain, inflammation, swelling, and bruising after dental procedures, compositions and methods of speeding up recovery after dental procedures and compositions and methods for maintaining oral health.

BACKGROUND

Oral health is essential for well-being (Petersen. The World Oral Health Report 2003 WHO/NMH/NPH/ORH/03.2 which is incorporated herein in its entirety). According to Petersen and The World Oral Health Report, oral health "implies being free of chronic oro-facial pain, oral and pharyngeal (throat) cancer, oral tissue lesions, birth defects such as cleft lip and palate, and other diseases and disorders that affect the oral, dental and craniofacial tissues, collectively known as the craniofacial complex." Moreover, proper oral health can reduce premature mortality and disease. Specifically, periodontal disease, for example, is associated with diabetes (Petersen. The World Oral Health Report 2003 WHO/NMH/NPH/ORH/03.2).

Oral health and hygiene are so fundamental in importance that international goals have been published, which include guidelines for minimizing the impact of oral diseases, reducing mortality from oral and craniofacial diseases, promoting sustainable policies for oral health systems, to developing accessible cost-effective health care systems, and reducing the disparities in oral health between individuals of different socio-economic backgrounds (Hobdell. Global goals for oral health 2020. International Dental Journal (2003) 53, 285-288 which is incorporated herein in its entirety.).

Poor oral health can lead to treatment procedures to remedy different dental problems and diseases. Facial swelling/edema and pain are common complications associated with oral surgery. These side effects along with bruising, trismus and inflammation affect the quality of a patients' life after the surgery. According to Pozzi et al. (Pozzi et al. Pain management for dentists: the role of ibuprofen. Ann Stomatol (Roma). 2011 Jul-Dec; 2(3-4 Suppl): 3-24. which is incorporated herein by reference in its entirety) "Alleviating pain is of the utmost importance when treating dental patients . . . " Techniques to reduce swelling, pain, and inflammation are available, but have certain drawbacks including negative reactions to certain types of analgesics. In particular, some patients may be allergic to nonsteroidal anti-inflammatory drug (NSAIDS). Different techniques for the management of pain and inflammation include corticosteroids and analgesics such as NSAIDs (Osunde et al. Management of inflammatory complications in third molar surgery: A review of the literature. Afr Health Sci. 2011 Sep.; 11(3): 530-537, which is incorporated herein by reference in its entirety). However, this review showed that no single modality of management effectively prevents the occurrence of these complications without undesirable side effects.

Removal of wisdom teeth is one of the most common procedures performed in oral and maxillofacial surgeons' offices. The most common postoperative complications of impacted lower third molar extractions are pain, trismus and facial swelling. (See, Goldberg et al. J Am Dent Assoc. 1985; 111:277, which is hereby incorporated by reference in its entirety) All these sequelae affect patient's recovery and influence his/her ability to resume normal daily activities. (See, Osborn et al. L J Oral Maxillofac Surg. 1985; 43:767; and White et.al. J OMS, 2003; Issue 5, pp 535-544, each of which is hereby incorporated by reference in its entirety) These symptoms usually peak 3-4 days after the surgery. Intraoperative and postoperative use of corticosteroids is a pharmacologic approach utilized commonly to reduce postoperative morbidity. The mechanism of their action is believed through inhibiting some initial steps of the inflammatory response to surgical injury. (See, Hooley et al. Trans Int Conf Oral Surg 4:188,1973; Hirschman, JV. Clin Exp Dermatol 11:27,1986; Seymour et al. Int J Oral Surg 13:457, 1984, each of which is hereby incorporated by reference in its entirety) However, their effect on post-operative morbidity varies. (See, Bystedt et al. Swed Dent J 9: 65,1985; and Edilby et al. J Dent Res 61:556, 1982, each of which is hereby incorporated by reference in its entirety)

Current therapies lack in efficacy. There is a need in the art for a reduction of post-surgical pain, inflammation, and trismus. Although other references speak to management of pain and inflammation during dental procedures, none teach the inventive formulation or treatment regime and outcomes as is presented herein.

*Arnica Montana* is a most commonly used homeopathic remedy today in setting of trauma, especially post-surgery. Its use in plastic surgery is wide spread. Brook M Seeley, et.al published the results of their randomized, double-blind, placebo-controlled study where they looked at the effect of *Arnica Montana* on bruising in face lifts. They found that patients taking perioperative homeopathic *A. Montana* exhibited less echhymosis, and that difference was statistically significant. (See, Seeley et.al Arch Facial Plast Surg. 2006; 8(1): 54-59, which is hereby incorporated by reference in its entirety) Other studies have yielded contradictory conclusion about its efficacy. (See, Kaziro et al. Br J Oral Maxillofac Surg 1984; 2242-49, which is hereby incorporated by reference in its entirety) *Arnica* is believed to increase the flow of blood around bruised tissue causing escaped fluids to be absorbed by the body. The absorption of the fluids reduces the swelling by relieving the pressure on nerve endings.

Goldstein et al. Unconventional Dentistry: Part IV. Unconventional Dental Practices and Products. J Can Dent Assoc 2000; 66:564-8 supports the use of homeopathic and herbal remedies in dentistry on page 5: "Dental promotions for homeopathy range from treatment of fear and anxiety, TMD, facial paralysis, aphthous ulcers, toothache, infections, bad breath and periodontal disease to counteracting the effects of mercury amalgam fillings and x-ray exposure, yet there is no evidence that homeopathy is effective for any dental use. Homeopathic remedies appear relatively benign and probably pose no significant risk for a basically healthy patient; however, irrational health care is not harmless."

U.S. Pat. No. 5,376,374 (Zelaya) teaches an oral rinse comprising " . . . Tincture of *Calendula officinalis* (active ratio 1/5, alcohol 65% by vol.) 56 milliliters, Tincture of

*capsicum frutescens* (cayenne pepper, active ratio 1/10, alcohol 75% by vol) 10 ml, Tincture of *Echinacea purpurea* and *echinacea angustifolia* (active ratio 1/1.8, alcohol 60% by vol). 56 ml, Tincture of *hydrastis canadensis* (goldenseal root, active ratio 1/5, alcohol 40% by vol.) 56 ml, Extract of propolis (alcohol-free, active ratio 1/10) 84 ml, Apple cider vinegar 486 ml, Distilled water 224 ml."

US 2009/0087501 (Cummins) teaches an oral composition comprising at least two ingredients from a long list of possible botanicals such as " . . . *Origanum vulgare, Origanum onites, Origanum majorana, Origanum heracleoticum, Thymus vulgaris L, Thymus citriodorus, Thymus pulegioides, Thymus* x herba-*barona, Thymus serpyllum, Lavandula angustifolia/officinalis, Lavandula stoechas, Lavandula dentate, Lavandula* x *intermedia, Lavandula multifida, Salvia officinalis, Salvia divinorum, Salvia apiana, Melissa Officinalis, Cuminum cyminum, Petroselinum crispum, Calendula arvensis, Calendula maderensis, Calendula officinalis, Tagetes erecta, Tagetes minuta, Tagetes patula, Boswellia sacra, Boswellia frereana, Boswellia serrata, Boswellia papyrifera, Sambucus nigra, Sambucus melanocarpa, Sambucus racemosa, Copaifera langsdorfii, Curcuma longa, Allium* sativu, *Symphytum officinale, Punica granatum, Euterpe oleracea, Sophora flavescens, Rheum rhabarbarum, Rheum rhaponticum, Fagopyrum esculentum, Camellia sinensis, Coptis teeta, Hydrastis canadensis, Mahonia aquifolium, Phellodendron amurense, Berberis vulgaris, Xanthorhiza simplicissima, Lonicera* ceprifoliu, *Vaccinium macrocarpon, Cinnamomum zeylanicum* Nees, *Cinnamomum verum, Vitis Vinifera, Terminalia* Billerica, *Pinus Pinaster, Albizia Lebbek, Melia Azadirachta, Salvadora persica, Paullinia cupana, Piper betle, Syzygium aromaticum, Commiphora myrrha, Juglans regia, Scutellaria baicalensis*, and *Magnolia officinalis* . . . and one or more of plants of the following species: Romains *officinalis, Origanum vulgare* L, *Thymus vulgaris* L, *Lavandula angustifolia/officinalis, Salvia officinalis, Melissa officinalis, Cuminum cyminum, Petroselinum crispum, Calendula officinalis, Tagetes erecta, Boswellia sacra, Sambucus nigra, Copaifera langsdorfii, Curcuma longa, Allium* sativu, *Symphytum officinale, Punica granatum, Euterpe oleracea, Sophora flavescens, Rheum rhabarbarum, Fagopyrum esculentum, Camellia sinensis, Coptis teeta, Hydrastis canadensis, Mahonia aquifolium, Phellodendron amurense, Berberis vulgaris, Xanthorhiza simplicissima, Lonicera* ceprifoliu, *Vaccinium macrocarpon, Cinnamomum zeylanicum* Nees, *Cinnamomum verum, Vitis Vinifera, Terminalia* Billerica, *Pinus Pinaster, Albizia Lebbek, Melia Azadirachta, Salvadora persica, Paullinia cupana, Piper betle, Syzygium aromaticum, Commiphora myrrha, Juglans regia, Scutellaria baicalensis*, and *Magnolia officinalis.*"

GB 1314136 to Grandel et al. calls out the use of *Azadirachta indica* specifically for applications in mouthwash.

U.S. Pat. No. 7,083,779 to Behl et al., incorporated herein by reference in its entirety, discusses " . . . a synergistic herbal formulation comprising an active fraction from *Azadirachta indica* designated as Fraction A and a fraction from *Citrullus colocynthis* designated as Fraction B, along with a fraction C containing an antioxidant from *Cucumis sativus* extract . . . "

A number of studies have looked at the effects of steroids on the post-operative swelling and pain. Grossi et.al. found nonsignificant reduction in post-op pain from submucosal injection of steroids during the surgical removal of third molars. (See, Nayyar, et al. Br J Oral Maxillofacial Surg. 2006; 44:501, which is hereby incorporated by reference in its entirety). Other studies have confirmed that steroids alone do not have a clinically significant analgesic effect. (See, Shugars et.al. J Oral Maxillofacial Surg 1996, 54: 1402-1408; and Grossi et.al. J Oral Maxillofacial Surg 2007, 65: 2218-2226, each of which is hereby incorporated by reference in its entirety) In fact, the use of steroids might increase the patient's reaction to pain by suppressing beta-endorphin levels. For example, Hargreaves et al. teaches that after the removal of impacted molars, . . . "all doses of dexamethasone suppressed the postoperative increase in circulating levels of immunoreactive β-endorphin. Patients administered 0.1 mg dexamethasone reported greater levels of pain, compared with those given placebo, from 60 through 120 minutes after surgery. Postoperative pain for the 0.32 and 1.0 mg doses did not differ from that for the placebo group. The increased pain after suppression of β-endorphin release by the low dose of dexamethasone suggests that pituitary secretion of immunoreactive β-endorphin alleviates postoperative pain under these conditions." (See, Miles et al. J Oral Maxillofac Surg 51: 987, 1993, which is hereby incorporated by reference in its entirety)

Therapeutic combinations can have different levels of efficacy and a practitioner must take care not to prescribe combinations that have lethal effects. Additionally, a practitioner must take care not to prescribe combinations that have little efficacy or combinations with contradictory outcomes.

Current therapies lack in efficacy and patient compliance. There is a need for better treatment, treatment that is more patient friendly and will encourage better patient compliance.

Homeopathics (HPUS) can help cure these needs. The basis for the regulation of homeopathic drugs in the United States can be found in the FDA Compliance Policy Guide 7132.15 "Conditions Under Which Homeopathic Drugs May Be Marketed," and the Homoeopathic Pharmacopoeia of the United States (HPUS). As part of its regulation of homeopathics, HPUS publishes standards and monographs of homeopathic substances. As per the HPUS, Drug Monographs encompass over 1300 official substances. Each monograph lists complete identifying data for the drug as well as specific manufacturing standards (http://www.hpus-.com/).

The present invention comprises active homeopathic ingredients which are based on HPUS monographs. The products are designed to decrease post-operative swelling, bruising and pain as well as pre-op and post-op anxiety. Moreover, the inventive product is administered in a patient friendly manner without the use of injections and without the need for practitioner visits. The patients can apply the remedy themselves which encourages patient compliance and positive outcomes. The three products utilize different routes of administration and work synergistically both locally and systemically to achieve maximum benefit.

To date, we do not have a single remedy that would reduce both swelling and pain, and speed up the post-surgical recovery as well as reduce anxiety associated with surgery, and be antimicrobial at the same time. Patients who take strong pain medications, like VICODIN® (Hydrocodone/Acetaminophen), are unable to return to their normal activities, including school and work. There is also currently a big issue with narcotic pain medications being overprescribed and a potential for abuse. The sooner the patient can stop taking pain medications, especially narcotics, the sooner they can return back to their everyday activities.

Therefore, there is a need in the art to promote anti-inflammatory, pain reducing, and wound healing effects after surgery and particularly after oral surgery.

BRIEF SUMMARY OF THE INVENTION

The present invention is directed to oral and/or dental care. Oral and/or dental care includes for example general oral maintenance, reduction of flora in the mouth, reduction of pain, reduction of inflammation, the reduction of bruising, trismus, recovery after dental surgeries, the amelioration of anxiety associated with dental care or preventative measures for maladies of the oral cavity. Maladies of the oral cavity include for example cavities/tooth decay, bone loss and periodontal pocket formation. In a healthy mouth, periodontal pockets should not be more than 3-4 mm or else proper care is not manageable. To that end, periodontal disease can begin when periodontal pockets are 5-7 mm deep.

One objective of the present invention is a formulation that alleviates pain, inflammation and/or trismus with a means for excellent patient compliance and a friendly application regiment.

A further objective of the present invention is a formulation that alleviates pain, inflammation and/or trismus, while treating anxiety associated with surgery with a means for excellent patient compliance and a friendly application regiment.

Another objective is to provide a formulation with no side effects, and free from any toxicity or toxic residue and irritation when regularly used.

Another objective is to provide a method of alleviating pain, inflammation and/or trismus, anxiety with better patient compliance and the application regime thereof is more patient friendly.

Still another object of the present invention is a kit comprising different formulations that alleviate pain, inflammation and/or trismus with a means for excellent patient compliance and a friendly application regiment. Another object of the present invention is a kit that is specifically designed to help patients recover more quickly after various dental/surgical procedures.

Still yet another object of the present invention is a kit comprising different formulations that alleviate pain, inflammation and/or trismus, anxiety with a means for excellent patient compliance and a friendly application regiment. Another object of the present invention is a kit that is specifically designed to help patients recover after various dental/surgical procedures while reducing the anxiety associated with surgery.

In still yet another embodiment of the present invention, the kit comprises a gel, a spray and a rinse which utilize different routes of administration and work synergistically both locally and systemically to achieve maximum benefit.

Another object of the present invention is a formulation for maintaining oral care and for the prevention of bone loss, tooth decay, cavities and loss of teeth.

In still another embodiment, the compositions disclosed herein may be combined with other treatment methods and substances including allopathic medicines, vitamins, minerals, amino acids, traditional homeopathic remedies, inert substances, etc.

In still yet another embodiment, the composition disclosed herein has antimicrobial properties. Years of experimentation and use of homeopathics has led to the inventive compositions herein.

Another object of the present invention is a homeopathic formulation for maintenance of oral care comprising Hepar sulphuris *calcareum, Calendula officinalis, Chamomilla, Aconitum napellus, Echinacea angustifolia, Echinacea purpurea, Ruta graveolens, Arnica montana, Mercurius vivus, Hypericum, Gelsemium, Ignatia amara* and optionally further comprising inactive ingredients, wherein the maintenance of oral care comprises general oral maintenance, reduction of flora in the mouth, reduction of pain in the oral cavity, reduction of inflammation in the oral cavity, reduction of edema in the oral cavity, the reduction of bruising in the oral cavity, the treatment of trismus, recovery after dental surgeries, pre-treatment prior to surgery pertaining to the oral cavity, the amelioration of anxiety associated with dental care or preventative measures for maladies of the oral cavity such as cavities, tooth decay, bone loss or periodontal pocket formation. The homeopathic formulation can be a spray or drops and the spray or drops can be part of a kit. The kit may further comprise a homeopathic gel formulation comprising Hepar sulphuris *calcareum, Calendula officinalis, Chamomilla, Aconitum napellus, Echinacea angustifolia, Echinacea purpurea, Ruta graveolens, Arnica montana, Mercurius vivus, Hypericum, Gelsemium, Ignatia amara* and optionally inactive ingredients. The kit may further comprise a homeopathic rinse formulation comprising *Calendula officinalis, Echinacea purpurea, Plantago major, Azadirachta indica* and optionally inactive ingredients.

Still yet another object of the present invention is a method of maintaining oral health wherein the maintaining of oral health comprises general oral maintenance, reduction of flora in the mouth, reduction of pain in the oral cavity, reduction of inflammation in the oral cavity, reduction of edema in the oral cavity, the reduction of bruising in the oral cavity, the treatment of post-surgical trismus, trismus, recovery after dental surgeries, pre-treatment prior to surgery pertaining to the oral cavity, the amelioration of anxiety associated with dental care or preventative measures for maladies of the oral cavity such as cavities, tooth decay, bone loss or periodontal pocket formation. The method may comprise a homeopathic formulation for maintenance of oral care comprising Hepar sulphuris *calcareum, Calendula officinalis, Chamomilla, Aconitum napellus, Echinacea angustifolia, Echinacea purpurea, Ruta graveolens, Arnica montana, Mercurius vivus, Hypericum, Gelsemium, Ignatia amara*, and optionally inactive ingredients.

Still another object of the present invention is a method of shortening the time to maximum pain, inflammation and/or trismus such that the post-surgical time to complete healing is shortened from 5 to 80% as compared to time to post-surgical time to healing with other homeopathic formulations. More preferably, post-surgical healing time is reduced by 30-50%.

Another object of the present invention is a method of promoting healing at a dental site.

Another object of the present invention is a method of reducing the number of post-operatively analgesics needed. Preferably, when used in combination with the present invention, the dosage of narcotics necessary for relief of post-surgical pain is reduced. In one embodiment, the narcotics need for alleviation of pain is 30-50% less when the formulation of the present invention is used to treat pain as compared to other medications.

DETAILED DESCRIPTION OF THE INVENTION

The present invention will now be described more fully hereinafter with reference to the accompanying figure, in which preferred embodiments of the invention are illustrated. This invention may, however, be embodied in different forms and should not be construed as limited to the embodiments set forth herein. Rather, these embodiments are provided so that this disclosure will be thorough and complete, and will fully convey the scope of the invention to those skilled in the art.

Homeopathic mother tinctures are made following monographs published by Homeopathic Pharmacopeia of the United States (HPUS). While plants are the base ingredients for most homeopathic tinctures, some are made from mineral, animal or other non-tangible substances. A homeopathic mother tincture, comprising base ingredients such as for example fresh plants and/or herbs, is generally prepared by extracting the ingredients in a suitable solvent. Suitable solvents include alcohol, water, water-alcohol mixtures, glycerine or isotonic sodium chloride solutions. Other parts of the extraction process may include the steps of comminution, maceration and squeezing according to accepted homeopathic pharmacopoeia.

As used herein, the term "tincture" refer to extracts of a part, combinations of parts and/or the entirety of an ingredient. The "tincture" can be prepared by exposing a part; parts and/or the entirety of the ingredient in a solvent, e.g. alcohol and/or water. The "tincture" of an ingredient preferably is a mother tincture of the ingredient prepared according to the procedures in the Homeopathic Pharmacopeia of the United States (HPUS), which is incorporated herein by reference in its entirety.

Original tinctures prepared according to HPUS can be called a mother tincture and are typically a 1× potency (1×10−1 dilution) according to the decimal scale. The mother tincture can be further diluted and/or succussed (further dilution with a solvent and then vigorously shaken). The dilution and succussion potencies are denoted as "X" or "D" for the decimal scale. There are other applicable scales that some practitioners use such as the centesimal and quintamillesimal scales. According to the decimal scale, each successive dilution will dilute the substance ten times its volume. For example, a 1× dilution has an ingredient to solvent ratio of 1:10, a 2× dilution has an ingredient to solvent ratio of 1:100, a 3× dilution has an ingredient to solvent ratio of 1:1000, a 4× dilution has an ingredient to solvent ratio of 1:10000, a 5× dilution has an ingredient to solvent ratio of 1:100000, a 6× dilution has an ingredient to solvent ratio of 1:1000000, a 7× dilution has an ingredient to solvent ratio of $1:10^7$, a 8× dilution has an ingredient to solvent ratio of $1:10^8$, a 9× dilution has an ingredient to solvent ratio of $1:10^9$, a 10× dilution has an ingredient to solvent ratio of $1:10^{10}$, a 11× dilution has an ingredient to solvent ratio of $1:10^{11}$, a 12× dilution has an ingredient to solvent ratio of $1:10^{12}$, a 13× dilution has an ingredient to solvent ratio of $1:10^{13}$, a 14× dilution has an ingredient to solvent ratio of $1:10^{14}$, a 15× dilution has an ingredient to solvent ratio of $1:10^{15}$, a 16× dilution has an ingredient to solvent ratio of $1:10^{16}$, a 17× dilution has an ingredient to solvent ratio of $1:10^{17}$, a 18× dilution has an ingredient to solvent ratio of $1:10^{18}$, a 19× dilution has an ingredient to solvent ratio of $1:10^{19}$, a 20× dilution has an ingredient to solvent ratio of $1:10^{20}$, a 21× dilution has an ingredient to solvent ratio of $1:10^{21}$, a 22× dilution has an ingredient to solvent ratio of $1:10^{22}$, a 23× dilution has an ingredient to solvent ratio of $1:10^{23}$, a 24× dilution has an ingredient to solvent ratio of $1:10^{24}$, a 25× dilution has an ingredient to solvent ratio of $1:10^{25}$, a 26× dilution has an ingredient to solvent ratio of $1:10^{26}$, a 27× dilution has an ingredient to solvent ratio of $1:10^{27}$, a 28× dilution has an ingredient to solvent ratio of $1:10^{28}$, a 29× dilution has an ingredient to solvent ratio of $1:10^{29}$, a 30× dilution has an ingredient to solvent ratio of $1:10^{30}$, a 31× dilution has an ingredient to solvent ratio of $1:10^{31}$, a 32× dilution has an ingredient to solvent ratio of $1:10^{32}$, a 33× dilution has an ingredient to solvent ratio of $1:10^{33}$, a 34× dilution has an ingredient to solvent ratio of $1:10^{34}$, a 35× dilution has an ingredient to solvent ratio of $1:10^{35}$, and so on. Table 1 below shows additional details for some of the potency levels.

TABLE 1

Examples of Decimal Homeopathic dilutions
Decimal

| Potency | Dilution | Concentration |
| --- | --- | --- |
| 1X or 1D | 1:10 | $10^{-1}$ |
| 2X or 2D | 1:100 | $10^{-2}$ |
| 3X or 3D | 1:1000 | $10^{-3}$ |
| 4X or 4D | 1:10000 | $10^{-4}$ |
| 5X or 5D | 1:100000 | $10^{-5}$ |
| 6X or 6D | 1:1000000 | $10^{-6}$ |
| 7X or 7D | 1:10000000 | $10^{-7}$ |
| 8X or 8D | 1:100000000 | $10^{-8}$ |
| 10X or 10D | 1:10000000000 | $10^{-10}$ |
| 12X or 12D | $1:10^{12}$ | $10^{-12}$ |
| 18X or 18D | $1:10^{18}$ | $10^{-18}$ |
| 30X or 30D | $1:10^{30}$ | $10^{-30}$ |

The homeopathic ingredients can be present in any amount that is safe and effective. The ingredients can be present in from dilutions from 1× to 40×. More preferably, the ingredients can be present in dilutions of 1×, 2×, 3×, 4×, 5×, 6×, 7×, 8×, 9×, 10×, 11×, 12×, 13×, 14×, 15×, 16×, 17×, 18×, 19×, 20×, 21×, 22×, 23×, 24×, 25×, 26×, 27×, 28×, 29×, 30×, 31×, 32×, 33×, 34×, 35×, 36×, 37×, 38×, 39×, or 40×.

I. Drops

In one embodiment, the present invention is a drop(s) comprising homeopathic ingredients. In one embodiment, the homeopathic drops comprise the following ingredients: Hepar sulphuris *calcareum* (also known as Calcium sulphide of Hahnemann, and sulphur of lime), *Calendula officinalis* (also known as, *Calendula* or *C. officinalis*), *Chamomilla* (also known as *Matricaria recutita* or chamomile), *Aconitum napellus* (also known as monkshood, aconite, wolfsbane, fuzi, monk's blood, or acon), *Echinacea angustifolia* (also known as or *Echinacea* or *E. angustifolia*), *Echinacea purpurea* (sometimes referred to as *Brauneria purpurea* (L.) Britton, *Helichroa purpurea* (L.) Raf. and/or Eastern purple coneflower), *Ruta graveolens* (also known as or rue or *R. graveolens*), *Arnica montana* (also known as or *arnica* or *A. montana*), *Mercurius vivus* (also known as Quicksilver), *Hypericum* (also known as St. John's wort), *Gelsemium*, *Ignatia amara* (also known as *ignatia*, *ignatia amara*, *samara*, *Strychnos ignatii*, or *S. ignatii*), and optionally inactive ingredients. The drops/spray gets absorbed systemically through sublingual mucosa. It acts systemically to decrease pain, swelling/edema including oral cavity. The use of the drops shorten the time to, duration of and duration of maximum pain, inflammation and/or trismus after a dental surgery. Additionally, when used in combination with VEGA™ rinse and gel, use of the drops after dental surgery reduce the needed dosage of narcotics when used in combination.

In another embodiment the homeopathic drops and/or spray comprise the following ingredients in the following amounts: Hepar sulphuris *calcareum* having a dilution of 8×, *Calendula officinalis* having a dilution of 3×, *Chamomilla* having a dilution of 5×, *Aconitum napellus* having a dilution of 3×, *Echinacea angustifolia* having a dilution of 3×, *Echinacea purpurea* having a dilution of 3×, *Ruta graveolens* having a dilution of 12×, *Arnica montana* having a dilution of 3×, 6×, 18×, *Mercurius vivus* having a dilution of 10×, *Hypericum* having a dilution of 10×, *Gelsemium* having a dilution of 30×, and *Ignatia amara* having a dilution of 30×.

II. Gel

In one embodiment, the present invention is a gel comprising homeopathic ingredients. In one embodiment, the homeopathic gel comprises the following ingredients: Hepar sulphuris *calcareum*, *Calendula officinalis*, *Chamomilla*, *Aconitum napellus*, *Echinacea angustifolia*, *Echinacea purpurea*, *Ruta graveolens*, *Arnica montana*, *Mercurius vivus*, *Hypericum*, *Gelsemium*, *Ignatia amara*, and optionally inactive ingredients. The gel can be used locally and have local effects. The gel can be applied topically. The gel can be applied directly on the oral mucosa. Moreover, the gel can get absorbed systemically as well and have systemic effects. The gel placed on the oral mucosa provides an alternative to injection into.

In another embodiment the homeopathic gel comprises the following ingredients in the following amounts: Hepar sulphuris *calcareum* having a dilution of 8×, *Calendula officinalis* having a dilution of 3×, *Chamomilla* having a dilution of 5×, *Aconitum napellus* having a dilution of 3×, *Echinacea angustifolia* having a dilution of 3×, *Echinacea purpurea* having a dilution of 3×, *Ruta graveolens* having a dilution of 12×, *Arnica montana* having a dilution of 3×, 6×, 18×, *Mercurius vivus* having a dilution of 10×, *Hypericum* having a dilution of 10×, *Gelsemium* having a dilution of 30×, and *Ignatia amara* having a dilution of 30×.

The gel has unique formula that allows direct delivery and absorption of active ingredients through oral mucosa. In the studies performed, it has shown to significantly reduce edema, pain and swelling associated with surgeries, provide immediate relief for Aphthous ulcers and cold sores.

III. Rinse

In one embodiment, the present invention is a rinse comprising homeopathic ingredients. In one embodiment, the homeopathic rinse comprises the following ingredients *Calendula officinalis*, *Echinacea purpurea*, *Plantago major*, *Azadirachta indica* (also known as Neem), and optionally inactive ingredients.

In one embodiment, the homeopathic rinse comprises the following ingredients in the following amounts: *Calendula officinalis* having a dilution of 1×, *Echinacea purpurea* having a dilution of 1×, *Plantago major* having a dilution of 1×, *Azadirachta indica* (also known as Neem) having a dilution of 1×, and optionally inactive ingredients.

The rinse was tested according to ASTM International Method E2315, Assessment of Antimicrobial Activity using a Time-Kill Procedure and the results can be found in Table 2 below.

TABLE 2

| | | | | | | | | |
|---|---|---|---|---|---|---|---|---|
| Antimicrobial Activity | | | | | | | | |
| Test Microorganism | Test Substance | Contact Time | Replicate | CFU/ml | Percent Reduction Compared to Control at Time Zero | Log10 Reduction Compared to Control at Time Zero | Average Percent Reduction | Average Log10 Reduction |
| S. mutans ATCC 25175 | VEGA™ Dental Rinse | Time | Initial Numbers Control | 3.95E+06 | N/A | N/A | 99.65% | 2.46 |
| | | Zero | 1 | 1.60E+04 | 99.59% | 2.39 | | |
| | | 45 Min | 2 | 1.10E+04 | 99.72% | 2.56 | | |

IV. Spray

In one embodiment, the present invention is a spray comprising homeopathic ingredients. In one embodiment, the homeopathic spray comprises the following ingredients: Hepar sulphuris *calcareum* (also known as Calcium sulphide of Hahnemann, and sulphur of lime), *Calendula officinalis* (also known as, *Calendula* or *C. officinalis*), *Chamomilla* (also known as *Matricaria recutita* or chamomile), *Aconitum napellus* (also known as monkshood, aconite, wolfsbane, fuzi, monk's blood, or aeon), *Echinacea angustifolia* (also known as or *Echinacea* or *E. angustifolia*), *Echinacea purpurea* (sometimes referred to as *Brauneria purpurea* (L.) Britton, *Helichroa purpurea* (L.) Raf. and/or Eastern purple coneflower), *Ruta graveolens* (also known as or rue or *R. graveolens*), *Arnica montana* (also known as or arnica or *A. montana*), *Mercurius vivus* (also known as Quicksilver), *Hypericum* (also known as St. John's wort), *Gelsemium*, *Ignatia amara* (also known as ignatia, ignatia amara, samara, *Strychnos ignatii*, or *S. ignatii*), and optionally inactive ingredients. The use of the spray shortens the time to, the intensity of and the duration of maximum pain, inflammation and/or trismus after a dental surgery. Additionally, when used in combination with VEGA™ rinse and gel described herein, the spray reduces the necessary dosage of narcotics when both are used in combination.

In another embodiment the homeopathic spray comprises the following ingredients in the following amounts: Hepar sulphuris *calcareum* having a dilution of 8×, *Calendula officinalis* having a dilution of 3×, *Chamomilla* having a dilution of 5×, *Aconitum* napellus having a dilution of 3×,

*Echinacea angustifolia* having a dilution of 3×, *Echinacea purpurea* having a dilution of 3×, *Ruta graveolens* having a dilution of 12×, *Arnica montana* having a dilution of 3×, 6×, 18×, *Mercurius vivus* having a dilution of 10×, *Hypericum* having a dilution of 10×, *Gelsemium* having a dilution of 30×, and *Ignatia amara* having a dilution of 30×.

In some instances, the formulation of the spray is identical to that of the drops except to the extent of the packaging. Therefore, the terms "spray" and "drop or drops" have the same meaning and can be used interchangeably unless otherwise indicated.

In other embodiments the invention is in a form of a solution, an oral tablet, pill, pillule, gel cap, syrup, elixir, suspension, emulsion, capsules, powders, globules, lozenges, aerosol, paste, film or pellets. Preferably, the inventive formulation is applied topically, which includes as non-limiting examples sublingually, as a rinse, as a gel, and/or any manner prescribed by a practitioner. The inventive formulation can be administered at a dosage amount, application time and regimen as prescribed by a practitioner.

In some embodiments, the present invention is a kit comprising a spray/drops/pallets, a gel and a rinse. In some embodiments, the present invention is a kit comprising a spray and a gel. In some embodiments, the present invention is a kit comprising a spray and a rinse. In some embodiments, the present invention is a kit comprising a gel and a rinse. In other embodiments, the present invention is a kit comprising drops, a gel, and a rinse. In some embodiments, the present invention is a kit comprising drops and a gel. In some embodiments, the present invention is a kit comprising drops and a rinse.

All of the spray, drops, gel and rinse can be packaged separately or together. Preferably, all of the spray (or drops), gel and rinse are individually packaged. More preferably, all of the spray (or drops), gel and rinse are individually contained and then packaged together as a kit.

The formulations can be applied prior to any surgical procedures, preferably any dental procedures. The formulations can, for example, be applied 5 days before surgery and every day up to surgery. The formulations can, for example, be applied 4 days before surgery and every day up to surgery. The formulations can, for example, be applied 3 days before surgery and every day up to surgery. The formulations can, for example, be applied 2 days before surgery and every day up to surgery. The formulations can, for example, be applied 1 day before surgery and every day up to surgery. The formulations can, for example, be applied prior to and the day of surgery.

The formulations can, for example, be applied the day after surgery and for 5 days post-surgery. The formulations can, for example, be applied the day after surgery and for 4 days post-surgery. The formulations can, for example, be applied the day after surgery and for 3 days post-surgery. The formulations can, for example, be applied the day after surgery and for 2 days post-surgery. The formulations can, for example, be applied post-operatively on the same day as surgery. More preferably, the formulations, can for example, be applied prior to, the day of and the day or days after surgery.

The formulations can, for example, be applied every day consecutively or can be applied as needed. The formulations can be used 1× a day. The formulations can be used 2× a day. The formulations can be used 3× a day. The formulations can be used 4× a day. The formulations can be used 5× a day. The dosage amounts and dosage routine of the each of the spray, gel and rinse can be the same or different.

In one embodiment, the kit comprising a spray, a gel and a rinse can have the following ingredients in the dilutions listed in Table 3 below.

TABLE 3

| Kit Components | | |
|---|---|---|
| DROPS/SPRAY | GEL | RINSE |
| *Hepar sulphuris calcareum* 8X, *Calendula officinalis* 3X, *Chamomilla* 5X, *Aconitum napellus* 3X, *Echinacea angustifolia* 3X, *Echinacea purpurea* 3X *Ruta graveolens* 12X *Arnica montana* 3X, 6X, 18X, *Mercurius vivus* 10X, *Hypericum* 10X, *Gelsemium* 30X, *Ignatia amara* 30X Inactive ingredients: citric acid, glycerin, potassium sorbate, purified water | *Hepar sulphuris calcareum* 8X, *Calendula officinalis* 3X, *Chamomilla* 5X, *Aconitum napellus* 3X, *Echinacea angustifolia* 3X, *Echinacea purpurea* 3X *Ruta graveolens* 12X, *Arnica montana* 3X, 6X, 18X, *Mercurius vivus* 10X, *Hypericum* 10X, *Gelsemium* 30X, *Ignatia amara* 30X Inactive ingredients: allantoin, hydroxyethylcellulose, peppermint oil, purified water, sodium benzoate, xylitol | *Calendula officinalis* 1X, *Echinacea purpurea* 1X, *Plantago major* 1X, *Azadirachta indica*/Neem 1X, Inactive ingredients: Xylitol, Allantoin, Peppermint oil, Glycerin, Citric acid, potassium sorbate, Purified Water, Polysorbate 20 |

Preferred inactive ingredients are citric acid, glycerin, potassium sorbate, and purified water. Other preferred inactive ingredients are allantoin, hydroxyethylcellulose, peppermint oil, purified water, sodium benzoate, and xylitol. Still other preferred inactive ingredients are Xylitol, Allantoin, Peppermint oil, Glycerin, Citric acid, Potassium sorbate, Purified Water, Polysorbate 20 and Poloxamer 407.

Other inactive ingredients may be any ingredient that forms a desirable consistency for the homeopathic ingredients. Inactive ingredients, such as excipients that are common to the health and/or cosmetic industries, as well as minerals, such as sea minerals can be used. Sea minerals, which can be included in the homeopathic formulation of the present invention include one or more of the following elements: Antimony, Barium, Beryllium, Bismuth, Boron, Bromine, Cadmium, Calcium, Carbonate, Cerium, Cesium, Chloride, Chromium, Cobalt, Copper, Dysprosium, Erbium, Europium, Gadolinium, Gallium, Germanium, Gold, Hafnium, Holmium, Indium, Iodine, Iridium, Iron, Lanthanum, Lead, Lithium, Lutetium, Magnesium, Manganese, Molybdenum, Neodymium, Nickel, Niobium, Osmium, Palladium, Phosphorus, Platinum, Potassium, Praseodymium, Rhenium, Rhodium, Rubidium, Ruthenium, Samarium, Scandium, Selenium, Silicon, Silver, Sodium, Strontium, Sulfate/Sulfur, Tantalum, Tellurium, Terbium, Thallium, Thorium, Thulium, Tin, Titanium, Tungsten, Vanadium, Ytterbium, Yttrium, Zinc, Zirconium, plus other naturally occurring trace minerals.

Preservatives such as potassium sorbate or silver can also be included in the homeopathic formulations.

The compositions herein taught might also be combined with surfactants and or items such as dimethyl sulfoxide (DMSO) that may assist, such as, in the penetration of the skin. Optional ingredients are those that when combined with the inventive products, result in the same cutaneous reduction of swelling, bruising, pain. Other examples of some excipients used in accordance with the invention are viscosity modifying agents, buffers, antioxidants, emulsifying agents, absorbents, antiacne agents, antiperspirants, anticaking agents, antifoaming agents, antimicrobial agents, anti-infective agents, antioxidants, antidandruff agents, astringents, binders, buffers, biological additives, buffering agents, bulking agents, chelating agents, chemical additives, coupling agents, conditioners, colorants, cosmetic astringents, cosmetic biocides, denaturants, drug astringents, detergents, dispersants, external analgesics, film formers, foaming agents, fragrance components, flavoring agents humectants, keratolytics, opacifying agents, pH adjusters, preservatives, propellants, proteins, retinoids, reducing agents, sequestrants, skin bleaching agents, skin-conditioning agents (humectants, miscellaneous, and occulsive), skin soothing agents, skin healing agents, softeners, solubilizing agents, lubricants, penetrants, plastisizers, solvents and co-solvents, sunscreening additives, sweeteners, salts, essential oils, and vitamins. In some embodiments, homeopathic formulations may include inactive ingredients ranging from about 0.01 wt % to about 95 wt % relative to the total weight of the formulation.

In another embodiment, the invention demonstrates antimicrobial properties.

The inventive formulations herein might also be administered simultaneously or during or instead of, treatment with prescription medications such as NORCO® (also known as VICODIN®, and wherein any reference to NORCO® throughout shall mean Hydrocodeine 5 mg/Acetominophen 325 mg), DECADRON® 8 mg IV at the time of the surgery, MOTRIN® 600 mg, and/or additional analgesics, steroids or the like considered appropriate by a skilled practitioner.

V. Preparation

The ingredients used to formulate the compositions of the present invention were obtained from plants, minerals or animal substances and are readily available at homeopathic pharmacies. The homeopathic ingredients can also be obtained from other sources such as online sources (http://www.hahnemannlabs.com/or http://www.swansonvitamins.com/). Each homeopathic remedy is attenuated using the decimal scale to the final potency ie: 3x, 5x, 9x etc. as described in the HPUS.

A spray formulation is made by combing homeopathic ingredients with the optional and/or inactive ingredients. For example, Hepar sulphuris *calcareum, Calendula officinalis, Chamomilla, Aconitum napellus, Echinacea angustifolia, Echinacea purpurea, Ruta graveolens, Arnica montana, Mercurius vivus, Hypericum, Gelsemium* and *Ignatia amara* are combined and mixed vigorously. Inactive ingredients, citric acid, glycerin, potassium sorbate and purified water, are then added and blended in the mixture.

An oral drops formulation is made by combing homeopathic ingredients with the optional and/or inactive ingredients. For example, Hepar sulphuris *calcareum, Calendula officinalis, Chamomilla, Aconitum napellus, Echinacea angustifolia, Echinacea purpurea, Ruta graveolens, Arnica montana, Mercurius vivus, Hypericum, Gelsemium* and *Ignatia amara* are combined and mixed vigorously. Inactive ingredients, citric acid, glycerin, potassium sorbate and purified water, are then added and blended in the mixture.

A gel formulation is made by preparing a homeopathic attenuation called the Mother Concentrate or Mother Tincture. A gel is further prepared by mixing purified water with hydroxyethyl cellulose to which the mother concentrate is added along with a sweetener, a skin conditioning, a flavoring agent and preservative. For example, a Mother concentrate is made with Hepar sulphuris *calcareum, Calendula officinalis, Chamomilla, Aconitum napellus, Echinacea angustifolia, Echinacea purpurea, Ruta graveolens, Arnica montana, Mercurius vivus, Hypericum, Gelsemium* and *Ignatia amara*. This Mother concentrate is then added to a mixture of purified water and hydroxyethyl cellulose. Finally, allantoin, hydroxyethylcellulose, peppermint oil, purified water, sodium benzoate and xylitol are then combined with the Mother concentrate, purified water and hydroxyethyl cellulose.

A dental rinse formulation is made by combing a Mother tincture with inactive ingredients and optional ingredients. For example, a Mother tincture will be a combination of *Calendula officinalis, Echinacea purpurea, Plantago major*, and *Azadirachta indica* (also known as Neem). Mother tinctures are then measured and combined in a large glass beaker. In another vessel, purified water, glycerin, allantoin and xylitol are mixed together until dissolved, the mother mixture is then added with more mixing, flavoring such as menthol or peppermint oil are dissolved in a solubilizing agent such as Poloxamer 407 or Polysorbate 20 and then added to the mixture and mixed until well combined and clear. Preservatives, for example citric acid and/or potassium sorbate, are then added and the PH adjusted.

Each of the spray, drops, gel and rinse formulations can be used together or separately.

The present invention is directed to oral and/or dental care. Oral and/or dental care includes for example general oral maintenance, reduction of flora in the mouth, reduction of pain, reduction of inflammation, the reduction of bruising, trismus, recovery after dental surgeries, the amelioration of anxiety associated with dental care or preventative measures for maladies of the oral cavity. Maladies of the oral cavity include for example cavities, tooth decay, bone loss and periodontal pocket formation.

The present invention is directed to a method of decreasing or reducing post-operative inflammation, edema, bruising, pain and related symptoms such as trismus after bodily insult and preferably after oral surgery. The active ingredient in the gel and drops (spray) have anti-anxiety property and are unique in a sense that we have anti-anxiety and pain/swelling/bruising properties all in one drug. Ignathia, which is the part of gel and drops, is called "homeopathic PROZAC™". The rinse has antimicrobial properties and has additive "antibiotic" properties.

The invention is now described with reference to the following Examples. These Examples are provided for the purpose of illustration only and the invention should in no way be construed as being limited to these Examples, but rather should be construed to encompass any and all variations that become evident as a result of the teaching provided herein.

EXAMPLES

Example 1

The purpose of this case report was to evaluate the anti-inflammatory and analgesic effects of VEGA™ drops, gel, and rinse (VEGA™ Recovery Kit) (VEGA™ Products in table below) after the surgical removal of four complete bony third molars. All patients were given VEGA™ products.

Methods: A group of 9 patients requiring removal of asymptomatic impacted third molars with ClassII/III position C impaction were selected. All of the patients satisfied the following selection criteria: ASA 1; Full bony impacted (ClassII/III position C) 4 third molars. All surgical procedures were performed by the same surgeon; no NSAIDS or steroids for at least a month prior to the study. To assess postoperative pain, visual analogue scales and consumption of post-op analgesics were used. The facial swelling and trismus were evaluated by measuring facial reference distances and maximum opening.

Results: Patients found to be mostly recovered on the fourth day post-op. The peak swelling was on the second post-operative day followed by a decrease almost back to the baseline on the fourth post-op day. Most of the patients required NORCO® for post-operative pain control for the first 2-3 days after the surgery. On the fourth post-operative day the swelling was reduced three-fold compared to the second post-operative day and was only 1% increase from the pre-operative baseline. Recovery for most HRQL measures, including pain occurred on post-operative day four. In contrast White R. P. et al published a study in which they looked at 630 patients undergoing third molar removal and reported the recovery for most HRQL measures occurred within five days after surgery. However, recovery from pain was delayed. By post-operative day seven, 15% of patients continued to report post-operative pain as severe, 5% reported post-operative pain as average. (See, White et.al. J OMS, 2003; Issue 5, pp 535-544, which is hereby incorporated by reference in its entirety)

Conclusion: VEGA™ products can provide alternative ways to control post-third molar recovery.

rinse) have fourteen active homeopathic ingredients including *arnica* in three different concentrations.

I. Dosage Instructions

Pre-Surgery Medication Instructions

Please follow these instructions beginning 3 days before your surgery and continuing for 7 days after your surgery:

1. Apply 15 VEGA™ Drops (Spray) under your tongue 4 times daily. Do not swallow for about 1 minute.

2. Apply VEGA™ Gel using a Q-TIP® applicator to the areas of all 4 wisdom teeth over the gum 3 times daily. Allow several minutes for the VEGA™ Gel to absorb. Do not rinse or eat for 20 minutes.

3. Swish with VEGA™ Rinse (10-15cc) three times daily for 2-3 minutes and then spit out the VEGA™ Rinse.

Day of Surgery Medication Instructions:

1. Take 4 Amoxicillin (500 mg/tablet) or Clindamycin (150 mg/tablet) tablets 1 hour before your surgery. You may take the pills with a glass of water.

Post-Surgery Instructions:

1. Continuing taking the VEGA™ Products (drops, gel, and rinse) as before surgery (see above).

2. Take Amoxicillin (500 mg/tablet) or Clindamycin (150 mg/tablet) tablets as prescribed three times a day until gone.

3. You may take NORCO® 5/325, 1-2 tablet every 4-6 hours. No MOTRIN® or other NSAIDs allowed. You do not have to take pain medications if no pain is experienced.

Patients

1. Total of nine patients, two males and 7 females participated. The age of the participants ranged between 17-21.

2. All patients received:
   2 gm of Amoxicillin 1 hr pre-op, and subsequent 5 days course of 500 mg tid
   NORCO® 5/325 mg (15 tabs).

Materials and Methods (1-4)

Facial swelling, trismus and pain were objectively measured on a post-op days 2, 4, and 7 by an independent examiner.

1. The facial swelling was measured by a tape measuring method. Four measurements were made between 6 reference points: tragus, lateral canthus of eye, pogonion, ala, gonion

TABLE 4

VEGA ™ Products

| DROPS/SPRAY | GEL | RINSE |
|---|---|---|
| *Hepar sulphuris calcareum* 8X, | *Hepar sulphuris calcareum* 8X, | *Calendula officinalis* 1X, |
| *Calendula officinalis* 3X, | *Calendula officinalis* 3X, | *Echinacea purpurea* 1X, |
| *Chamomilla* 5X, | *Chamomilla* 5X, | *Plantago major* 1X, |
| *Aconitum napellus* 3X, | *Aconitum napellus* 3X, | *Azadirachta indica*/Neem 1X, |
| *Echinacea angustifolia* 3X, | *Echinacea angustifolia* 3X, | Inactive ingredients: Xylitol, |
| *Echinacea purpurea* 3X | *Echinacea purpurea* 3X | Allantoin, Peppermint oil, Glycerin, |
| *Ruta graveolens* 12X, | *Ruta graveolens* 12X, | Citric acid, potassium sorbate, |
| *Arnica montana* 3X, 6X, 18X, | *Arnica montana* 3X, 6X, 18X, | Purified Water, Polysorbate 20 |
| *Mercurius vivus* 10X, | *Mercurius vivus* 10X, | |
| *Hypericum* 10X, | *Hypericum* 10X, | |
| *Gelsemium* 30X, | *Gelsemium* 30X, | |
| *Ignatia amara* 30X | *Ignatia amara* 30X | |
| Inactive ingredients: citric acid, glycerin, potassium sorbate, purified water | Inactive ingredients: allantoin, hydroxyethylcellulose, peppermint oil, purified water, sodium benzoate, xylitol | |

This case report was performed to look into the use of homeopathic—based remedies applied both locally and systemically to reduce postoperative swelling and pain after third molar surgery. VEGA™ products (spray/drops, gel and and the corner of the mouth. The post-op sum of the measurements was considered as the baseline for that side.

2. Mouth opening, taken as the maximum distance between upper and lower central incisors was measured by the ruler to the nearest mm. Pre-op value was recorded. Post-op Trismus was measured the same way on days 2, 4 and 7.

3. Post-operative pain was recorded by having the patient report the number of analgesic tablets required. Post-operative pain was rated daily for 7 days using a 100-point visual analog scale (VAS) anchored by the verbal descriptors "no pain"(0) and "very severe pain" (10).

4. After surgery, each patient was given the HRQOL (also shown herein as Health-Related Quality of Life or HRQL) instrument or a diary as described by Shugars et al (J Oral Maxillofacial Surg 1996, 54: 1402-1408). HRQOL data were collected from the patients on daily bases for 7 days after the procedure. (See, White et.al. J OMS, 2003; Issue 5,pp 535-544; Kim et.al. 000, 2006;102:e4; Bouloux et al. J Oral Maxillofacial Surg. 1999; 57:510; Esen et al. J Oral Maxillofacial Surg. 1999;57: 1201; Nayyar et al. Br J Oral Maxillofacial Surg. 2006; 44:501.; and Shugars et al. J Oral Maxillofacial Surg 1996, 54: 1402-1408, each of which are hereby incorporated by reference in its entirety).

Figure 2:
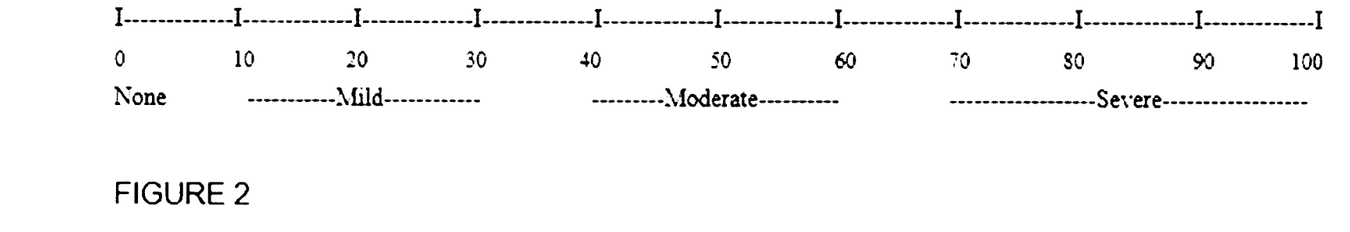
FIG. 2 is a 100-point visual analog scale (VAS). Indications for the severity of pain begin at 0 which is considered no pain and end at 100 which is considered the worst pain. Pain levels between about 10 to about 30 are indicative of a range of mild pain, pain levels between about 40 to about 60 are indicative of a range of moderate pain, and pain levels between about 70 to 100 are indicative of a range of severe pain.

Post-operative pain was rated daily for 7 days using a 100-point visual analog scale (VAS). Indications for the severity of pain begin at 0 which is considered no pain and end at 100 which is considered the worst pain. Pain levels between about 10 to about 30 are indicative of a range of mild pain, pain levels between about 40 to about 60 are indicative of a range of moderate pain, and pain levels between about 70 to 100 are indicative of a range of severe pain, as shown in FIG. 2.

II. Results

In this study, we looked at the use of alternative methods to decrease swelling and pain after removal of impacted third molars. Based on our data, on the post-op day 3 the patients required less than 1 NORCO® (Hydrocodone5/Actominophen325) pain pill. On the post-operative day 4 the swelling was three times less compared to the second day post-op and was only 1% increase from the pre-op baseline. Recovery for most health-related quality of life (HRQL) measures, including pain, has occurred on the post-op day 4. By comparison, White R. P. et al. published a study (which is incorporated herein in its entirety) in which they looked at 630 patients undergoing third molar removal. However, the reference suggests that over-the-counter and prescribed medications were taken by the patients and not homeopathics. Similarly to our case report, the patients selected fell in the same age range. They reported that in their study the recovery for most HRQL measures occurred within 5 days after surgery. However, recovery from pain was delayed. By post-surgery day 7, 15% of patients still reported their pain as severe; 5% reported average pain as severe. (See, White et.al. J OMS, 2003; Issue 5, pp 535-544, which is hereby incorporated in its entirety)

TABLE 5

Daily Pain Measurements

| | DAY 1 | DAY 2 | DAY 3 | DAY 4 | DAY 5 | DAY 6 | DAY 7 |
|---|---|---|---|---|---|---|---|
| Severity (Patient) | 73.375 | 51.23 | 49.25 | 38.38 | 29.63 | 20 | 10 |
| Severity (Clinician) | | 57.63 | | 37 | | | 14 |
| Intensity (Patient) | 58.88 | 40.13 | 36.13 | 29.13 | 21.63 | 13.25 | 8.5 |
| Intensity (Clinician) | | 46.63 | | 26.25 | | | 9.75 |

TABLE 6

Pain Management

| Days Post Op | DAY 1 | DAY 2 | DAY 3 | DAY 4 | DAY 5 | DAY 6 | DAY 7 |
|---|---|---|---|---|---|---|---|
| avg # NORCO ® pills | 3.5 | 2.3 | 0.8 | 0.6 | 0.5 | 0.4 | 0.25 |

TABLE 7

Trismus/Mouth Opening

| Days Post Op | Pre-Op | DAY 2 | DAY 4 | Day 7 |
|---|---|---|---|---|
| mm | 49 | 22.56 | 29.89 | 39.78 |
| % trismus | | 46% | 61% | 81.20% |

TABLE 8

Swelling

| Days Post Op | Pre-Op | DAY 2 | DAY 4 | Day 7 |
|---|---|---|---|---|
| MM | 913.75 | 944.88 | 922.75 | 915.63 |
| % | | 103 3% | 101 1% | 100.2 0.2 |

Example 2

Post-Surgical Management after Various Periodontal Surgical Procedures.

Background: a series of twenty case reports evaluated the effects of VEGA™ Oral Gel and Rinse as adjunctive therapy for post-surgical management after pocket reduction osseous surgery, connective tissue grafting, extraction and site preservation bone graft.

Methods: Twenty patients, not on medication, went through pocket reduction osseous surgery, connective tissue grafting, extraction and/or site preservation bone graft. VEGA™ Gel and Rinse were applied on only one side in the split mouth designs after pocket reduction osseous surgery. On the other side of the mouth, either PERIDEX® rinse (chlorhexidine gluconate 0.12%) or an AO PERIOSCIENCE® Rinse was applied.

Results: on day three less swelling was observed on the VEGA™ treated side than on the side treated with either the PERIDEX® rinse (chlorhexidine gluconate 0.12%) or the AO PERIOSCIENCE® Rinse.

Conclusion: patients unanimously reported having less problems with the VEGA™ treated side than on the side treated with either the PERIDEX® rinse (chlorhexidine gluconate 0.12%) or the AO PERIOSCIENCE® Rinse.

Comments: Many enjoyed the taste of the Stellalife™ products and wished to purchase it. This was reported by almost every patient and was unprompted.

Comparative Example 1

A study is conducted to determine the reduction of periodontal pocket depth in patients with moderate periodontal disease who underwent deep scaling and root planning. The pockets are measured before treatment. A split mouth study design is used. A study is conducted to determine the reduction of periodontal pocket depth after 1 month of VEGA™ gel and rinse product application to the gums and compared to the control side. Patients are instructed to apply the VEGA™ rinse and gel twice a day with a Q-TIP" applicator to the gums and base of teeth on one side of the mouth for one month. Chlorhexidine is applied once daily to the other side of the mouth. After 1 month, the side of the mouth to which VEGA™ rinse/gel are applied shows a reduction in periodontal pocket depth of 1-2 mm more then on the control side.

Comparative Example 2 [*ARNICA* AND NORCO®]

The purpose of this case report is to evaluate the anti-inflammatory and analgesic effects of *arnica* after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All patients are given *arnica*. The *arnica* regimen is to take 4 pallets under the tongue 4×/day. Patients are instructed to begin *arnica* regimen 3 days pre-op and continue regimen through the seventh day post-op. All surgical procedures are performed by the same surgeon; no NSAIDS or steroids are taken for at least a month prior to the study. To assess postoperative pain, visual analogue scales and consumption of post-op analgesics are used. The facial swelling and trismus are evaluated by measuring facial reference distances and maximum opening.

Results: Patients are found to be mostly recovered on the sixth-seventh day post-op. The peak swelling is on the fourth post-operative day, following by decrease almost back to the baseline on the sixth to seventh post-op day. Most of the patients require NORCO® for post-operative pain control for the first 7 days after the surgery.

TABLE 9

| NORCO ® pain management | | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 2 | 1 | 1 | 1 |

Conclusion: *Arnica* does not control post-third molar recovery as compared to Vega™ products.

This case report is performed to look into the use of homeopathic based remedies applied both locally and systemically to reduce postoperative swelling and pain after third molar surgery.

Patients, Materials and methods were the same as in Example I.

Comparative Example 3 [TRAUMEEL® AND NORCO®]

The purpose of this case report is to evaluate the anti-inflammatory and analgesic effects of TRAUMEEL® after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All patients are given TRAUMEEL®. The TRAUMEEL® regimen is to take 3 pallets under the tongue 4×/day. Patients are instructed to begin TRAUMEEL® regimen 3 days pre-op and continue regimen through the seventh day post-op. All surgical procedures are performed by the same surgeon; no NSAIDS or steroids are taken for at least a month prior to the study. To assess postoperative pain, visual analogue scales and consumption of post-op analgesics are used. The facial swelling and trismus are evaluated by measuring facial reference distances and maximum opening.

Results: Patients are found to be mostly recovered on the sixth-seventh day post-op. The peak swelling is on the fourth post-operative day, following by decrease almost back to the baseline on the 7th post-op day. Most of the patients require NORCO® for post-operative pain control all 7 days after the surgery.

TABLE 10

| NORCO ® pain management | | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 3 | 1-2 | 1 | 1 |

Conclusion: when combined with prescription narotic analgesics, TRAUMEEL® does not control post-third molar recovery as compared to VEGA™ products.

This case report is performed to look into the use of homeopathic—based remedies applied both locally and systemically to reduce postoperative swelling and pain after third molar surgery.

Patients, Materials and methods were the same as in Example 1.

Comparative Example 4 [*ARNICA* AND NORCO® AND MOTRIN®]

The purpose of this case report is to evaluate the anti-inflammatory and analgesic effects of *Arnica* and MOTRIN® combination as compared to VEGA™ Recovery Kit after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All surgical procedures are performed by the same surgeon; no NSAIDS or steroids are taken for at least a month prior to the study. All patients are given *arnica*. The *arnica* regimen is to take 4 pallets under the tongue 4×/day. Patients are instructed to begin *arnica* regimen 3 days pre-op and continue regimen through the seventh day post-op. To assess postoperative pain, visual analogue scales and consumption of post-op analgesics are used. The facial swelling and trismus are evaluated by measuring facial reference distances and maximum opening.

Results: Patients are found to be mostly recovered on the sixth day post-op. The peak swelling is on the fourth post-operative day, following by decrease almost back to the baseline on the 7th post-op day. Most of the patients require NORCO® for post-operative pain control all 7 days after the surgery.

TABLE 11

| NORCO ® pain management | | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 2 | 1 | 0.5 | 0.5 |

Conclusion: *Arnica* and MOTRIN® as a combination do not control post-third molar recovery as compared to VEGA™ products.

This case report is performed to look into the use of homeopathic—based remedies applied both locally and systemically to reduce postoperative swelling and pain after third molar surgery.

Materials and methods were the same as in Example 1.
Patients

Total of nine patients, two males and 7 females participate. The age of the participants ranges between 17-21.

All Patients Additionally Receive:
1. 2 gm of Amoxicillin 1 hr pre-op, and subsequent 5 days course of 500 mg tid
2. NORCO® 5/325 mg (15 tabs)
3. MOTRIN® 600 mg Comparative Example 5 [TRAUMEEL® AND NORCO® AND MOTRIN®]

The purpose of this case report is to evaluate the anti-inflammatory and analgesic effects of TRAUMEEL® and MOTRIN® combination as compared to VEGA™ Recovery Kit after the surgical removal of four complete bony third molars. Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All surgical procedures are performed by the same surgeon; no NSAIDS or steroids are taken for at least a month prior to the study. All patients are given TRAUMEEL®. The TRAUMEEL® regimen is to take 3 pallets under the tongue 4x/day. Patients are instructed to begin TRAUMEEL® regimen 3 days pre-op and continue regimen through the seventh day post-op. To assess postoperative pain, visual analogue scales and consumption of post-op analgesics are used. The facial swelling and trismus are evaluated by measuring facial reference distances and maximum opening.

Results: Patients are found to be mostly recovered on the sixth day post-op. The peak swelling is on the fourth post-operative day, following by decrease almost back to the baseline on the 6th post-op day. Most of the patients require NORCO® for post-operative pain control all 7 days after the surgery.

TABLE 12

| NORCO ® pain management | | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 2 | 1 | 0.5 | 0.5 |

Conclusion: TRAUMEEL® and MOTRIN® as a combination does not control post-third molar recovery as compared to VEGA™ products.

This case report is performed to look into the use of homeopathic—based remedies applied both locally and systemically to reduce postoperative swelling and pain after third molar surgery.

Materials and methods were the same as in Example 1.
Patients

Total of nine patients, two males and 7 females participate. The age of the participants ranges between 17-21.

All Patients Additionally Receive:
1. 2 gm of Amoxicillin 1 hr pre-op, and subsequent 5 days course of 500 mg tid
2. NORCO® 5/325 mg (15 tabs).
3. MOTRIN® 600 mg Comparative Example 6 [*ARNICA* AND NORCO® AND DECADRON®]

The purpose of this case report is to evaluate the anti-inflammatory and analgesic effects of *arnica* after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All surgical procedures are performed by the same surgeon; no NSAIDS or steroids are taken for at least a month prior to the study. All patients are given *arnica*. The *arnica* regimen is to take 4 pallets under the tongue 4x/day. Patients are instructed to begin *arnica* regimen 3 days pre-op and continue regimen through the seventh day post-op. To assess postoperative pain, visual analogue scales and consumption of post-op analgesics are used. The facial swelling and trismus are evaluated by measuring facial reference distances and maximum opening.

Results: Patients are found to be mostly recovered on the sixth day post-op. The peak swelling is on the fourth post-operative day, following by decrease almost back to the baseline on the seventh post-op day.

TABLE 13

| NORCO ® pain management | | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 2 | 1 | 1 | 0.5-1 |

Conclusion: *Arnica* and DECADRON® as a combination do not control post-third molar recovery as compared to VEGA™ products.

This case report is performed to look into the use of homeopathic—based remedies applied both locally and systemically to reduce postoperative swelling and pain after third molar surgery.

Materials and methods were the same as in Example 1.
Patients

Total of nine patients, two males and 7 females participate. The age of the participants ranges between 17-21.

All Patients Additionally Receive:
1. 2 gm of Amoxicillin 1 hr pre-op, and subsequent 5 days course of 500 mg tid 2. NORCO® 5/325 mg (15 tabs).
3. DECADRON® 8 mg IV— administered once during the surgery.

Comparative Example 7 [TRAUMEEL® AND NORCO® AND DECADRON®]

The purpose of this case report is to evaluate the anti-inflammatory and analgesic effects of TRAUMEEL® after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All surgical procedures are performed by the same surgeon; no NSAIDS or steroids are taken for at least a month prior to the study. All patients are given TRAUMEEL®. The TRAUMEEL® regimen is to take 3 pallets under the tongue 4x/day. Patients are instructed to begin TRAUMEEL® regimen 3 days pre-op and continue regimen through the seventh day post-op. To assess postoperative pain, visual analogue scales and consumption of post-op analgesics are used. The facial swelling and trismus are evaluated by measuring facial reference distances and maximum opening.

Results: Patients are found to be mostly recovered on the sixth day post-op. The peak swelling is on the fourth post-operative day, following by decrease almost back to the baseline on the sixth post-op day.

TABLE 14

| | NORCO ® pain management | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 2 | 1 | 1 | 0.5-1 |

Conclusion: TRAUMEEL® and DECADRON® as a combination do not control post-third molar recovery as compared to VEGA™ products.

This case report is performed to look into the use of homeopathic-based remedies applied both locally and systemically to reduce postoperative swelling and pain after third molar surgery.

Materials and methods were the same as in Example 1.
Patients
Total of nine patients, two males and 7 females participate. The age of the participants ranges between 17-21.
All Patients Additionally Receive:
1. 2 gm of Amoxicillin 1 hr pre-op, and subsequent 5 days course of 500 mg tid
2. NORCO® 5/325 mg (15 tabs).
3. DECADRON® 8 mg IV— administered once during the surgery.

Comparative Example 8 [*Arnica* and NORCO® and DECADRON® AND MOTRIN®]

The purpose of this case report is to evaluate the anti-inflammatory and analgesic effects of *arnica* after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All surgical procedures are performed by the same surgeon; no NSAIDS or steroids are taken for at least a month prior to the study. All patients are given *Arnica*. The *Arnica* regimen is to take 4 pallets under the tongue 4x/day. Patients are instructed to begin *Arnica* regimen 3 days pre-op and continue regimen through the seventh day post-op. To assess postoperative pain, visual analogue scales and consumption of post-op analgesics are used. The facial swelling and trismus are evaluated by measuring facial reference distances and maximum opening.

Results: Patients are found to be mostly recovered on the fifth-sixth day post-op. The peak swelling is on the third post-operative day, following by decrease almost back to the baseline on the 6th post-op day. Most of the patients require NORCO® for post-operative pain control all 7 days after the surgery.

TABLE 15

| | NORCO ® pain management | | | | | | |
|---|---|---|---|---|---|---|---|
| Days Post Op | DAY 1 | DAY 2 | DAY 3 | DAY 4 | DAY 5 | DAY 6 | DAY 7 |
| avg # NORCO ® pills | 4 | 4 | 3 | 2 | 1 | 0.5 | 0.25 |

Conclusion: *Arnica*, DECADRON®, NORCO® AND MOTRIN® as a combination do not control post-third molar recovery as compared to VEGA™ products Materials and methods were the same as in Example 1.
Patients
Total of nine patients, two males and 7 females participate. The age of the participants ranges between 17-21.
All Patients Additionally Receive:
1. 2 gm of Amoxicillin 1 hr pre-op, and subsequent 5 days course of 500 mg tid
2. NORCO® 5/325 mg (15 tabs).
3. MOTRIN® 600 mg
4. DECADRON® 8 mg IV— administered once during the surgery.

Comparative Example 9 [TRAUMEEL® and NORCO® DECADRON® AND MOTRIN®]

The purpose of this case report is to evaluate the anti-inflammatory and analgesic effects of TRAUMEEL® after the surgical removal of four complete bony third molars.

Methods: A group of 9 patients requiring removal of asymptomatic impacted third molars with ClassII/III position C impaction is selected. All of the patients satisfy the following selection criteria: ASA I; Full bony impacted (ClassII/III position C) 4 third molars. All surgical procedures are performed by the same surgeon; no NSAIDS or steroids are taken for at least a month prior to the study. All patients are given TRAUMEEL®. The TRAUMEEL® regimen is to take 3 pallets under the tongue 4x/day. Patients are instructed to begin TRAUMEEL® regimen 3 days pre-op and continue regimen through the seventh day post-op. To assess postoperative pain, visual analogue scales and consumption of post-op analgesics are used. The facial swelling and trismus are evaluated by measuring facial reference distances and maximum opening.

Results: Patients are found to be mostly recovered on the sixth day post-op. The peak swelling is on the third postoperative day, following by decrease almost back to the baseline on the 7th post-op day. Most of the patients require NORCO® for post-operative pain control all 7 days after the surgery.

TABLE 16

NORCO ® pain management

| Days Post Op | DAY 1 | DAY 2 | DAY 3 | DAY 4 | DAY 5 | DAY 6 | DAY 7 |
|---|---|---|---|---|---|---|---|
| avg # NORCO ® pills | 4 | 4 | 3 | 2 | 1 | 0.5 | 0.25 |

3. MOTRIN® 600 mg
4. DECADRON® 8 mg IV— administered once during the surgery.

Comparison Table

Figure 1:
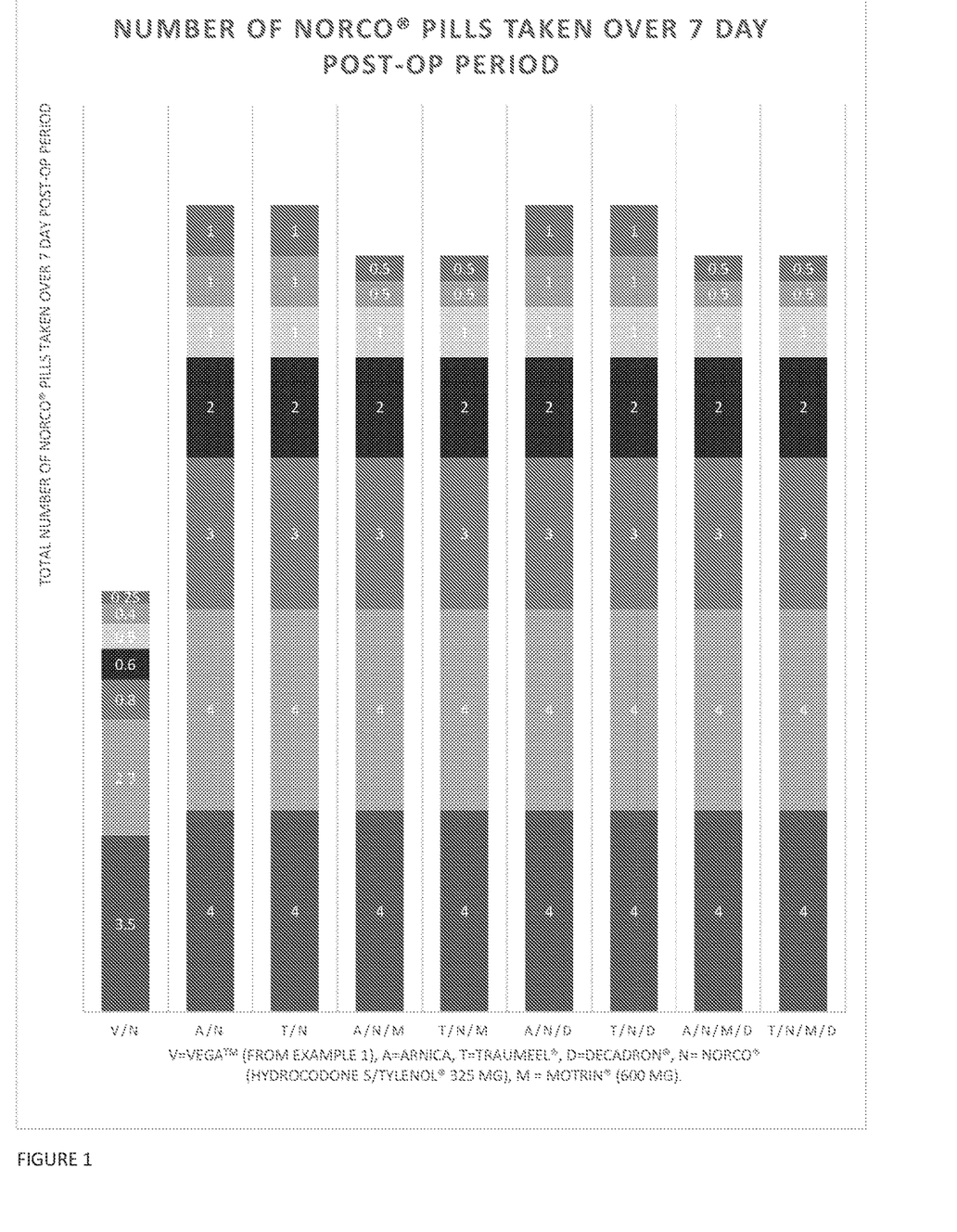
FIG. 1 is a graphical representation of the average number of NORCO® pills required post surgically as a result of the treatment of Example 1.

The table below, as well as the graphical representation of similarly representative data shown in FIG. 1, shows representative data from Example 1 and Comparative Examples 2-9 above. It was surprisingly found that the number of NORCO® pills needed by the patients who were treated with VEGA™ products were reduced as compared to those patients who were treated with other homeopathics, steroids, and/or NSAIDS. As can be seen from the table, the number of NORCO® pills required is markedly reduced by day 3 and that the recovery from surgery is accelerated. Moreover, the time to peak swelling is accelerated as well.

TABLE 17

Comparison Table

| Treatment | Number of NORCO ® pills taken days 1-7 post-op | | | | | | | Day of peak swelling | Day of full recovery |
| | Day 1 post-op | Day 2 post-op | Day 3 post-op | Day 4 post-op | Day 5 post-op | Day 6 post-op | Day 7 post-op | | |
|---|---|---|---|---|---|---|---|---|---|
| V(Drops/Gel/Rinse)/N | 3.5 | 2.3 | 0.8 | 0.6 | 0.5 | 0.4 | 0.25 | Peak-1D-2D | Recovery-$3^{rd}$-4th |
| A/N | 4 | 4 | 3 | 2 | 1 | 1 | 0.5-1 | Peak-4D | Recovery-$6^{th}$-7th |
| T/N | 4 | 4 | 3 | 2 | 1 | 1 | 0.5-1 | Peak-4D | Recovery-$6^{th}$-7th |
| A/N/M | 4 | 4 | 3 | 2 | 1 | 0.5 | 0.5 | Peak-4D | Recovery-$6^{th}$-7th |
| T/N/M | 4 | 4 | 3 | 2 | 1 | 0.5 | 0.5 | Peak-4D | Recovery-6th |
| A/N/D | 4 | 4 | 3 | 2 | 1 | 1 | 0.5-1 | Peak-4D | Recovery-$6^{th}$-7th |
| T/N/D | 4 | 4 | 3 | 2 | 1 | 1 | 0.5-1 | Peak-4D | Recovery-$6^{th}$-7th |
| A/N/M/D | 4 | 4 | 3 | 2 | 1 | 0.5 | 0.5 | Peak-3D | Recovery-$5^{th}$-6th |
| T/N/M/D | 4 | 4 | 3 | 2 | 1 | 0.5 | 0.5 | Peak-3D | Recovery-$5^{th}$-6th |

V = VEGATM (from Example 1),
A = arnica,
T = TRAUMEEL ®,
D = DECADRON ®,
N = NORCO ® (Hydrocodone 5/Tylenol 325 mg),
M = MOTRIN ® (600 mg).

Conclusion: DECADRON®, NORCO® AND MOTRIN® as a combination with TRAUMEEL® do not control post-third molar recovery as compared to VEGA™ products.

Materials and methods: same as in Example 1

Patients

Total of nine patients, two males and 7 females participate. The age of the participants ranges between 17-21.

All Patients Additionally Receive:

1. 2 gm of Amoxicillin 1 hr pre-op, and subsequent 5 days course of 500 mg tid
2. NORCO® 5/325 mg (15 tabs).

Comparison Table

The number of NORCO® pills taken by patients in Examples 1, Comparative Example 2 and Comparative Example 3 are compared in Table 18 below.

TABLE 18

Comparison of the number of NORCO ® pills taken by patients

| Comparative Example | Day 1 post-op | Day 2 post-op | Day 3 post-op | Day 4 post-op | Day 5 post-op | Day 6 post-op | Day 7 post-op |
|---|---|---|---|---|---|---|---|
| 1 | 3.5 | 2.3 | 0.8 | 0.6 | 0.5 | 0.4 | 0.25 |
| 2 | 4 | 4 | 3 | 2 | 1 | 1 | 0.25 |
| 3 | 4 | 4 | 3 | 3 | 1.5 | 1 | 0.5 |

It can be seen that when patients are receiving VEGA™ as in Example 1, the number of NORCO® pills required is sharply less as compared to Comparative Example 2 wherein patients are administered *Arnica* and Comparative Example 3 wherein patients are administered TRAUMEEL®. Moreover, the time required to reach peak swelling post-operatively is sharply reduced with the patients receiving VEGA™ products. This can be seen in Table 19 below.

TABLE 19

Number of days to peak swelling

| Treatment | Number of days |
|---|---|
| V/N | 1 |
| A/N | 4 |
| T/N | 4 |
| A/N/M | 4 |
| T/N/M | 4 |
| A/N/D | 4 |
| T/N/D | 4 |
| A/N/M/D | 3 |
| T/N/M/D | 3 |

It was surprising that there was a marked decrease in the number of days required for a full recovery post-operatively between the patients who received VEGA™ products and those that did not. The following graph compares the number of days required for a full recovery between patients receiving VEGA™ products and patients receiving other combinations of analgesics, steroids, homeopathics and/or NSAIDS.

TABLE 20

Number of days to full recovery

| Treatment | Number of days |
|---|---|
| V/N | 4 |
| A/N | 7 |
| T/N | 7 |
| A/N/M | 7 |
| T/N/M | 6 |
| A/N/D | 7 |
| T/N/D | 7 |
| A/N/M/D | 6 |
| T/N/M/D | 6 |

The oral mucosa is the mucous membrane lining the inside of the mouth and consists of stratified squamous epithelium termed oral epithelium and an underlying connective tissue termed lamina propria. IgA found therein has a role in protecting against microbes and is an immunological regulator (http://en.wikipedia.org/wiki/Immunoglobulin A).

Oral mucosa heals differently than non-mucosal epidermis (Chen et al. Positional differences in the wound transcriptome of skin and oral mucosa. Chen et al. BMC Genomics 2010, 11:471). Oral mucosal tissues contains much less inflammatory potential than skin since they contain less cytokines involved in the inflammatory process. IL-lb and TNF-α, for example are reduced in oral mucosal tissue. As used herein "mucosal layer" means any mucous membranes (or mucosae, mucosas, or mucosa) or mucosal tissue.

The term "about" or "approximately" means within an acceptable error range for the particular value as determined by one of ordinary skill in the art, which will depend in part on how the value is measured or determined, i.e., the limitations of the measurement system. For example, "about" with respect to the compositions can mean plus or minus a range of up to 20%, preferably up to 10%, more preferably up to 5%. Alternatively, particularly with respect to biological systems or processes, the term can mean within an order of magnitude, preferably within 5-fold, and more preferably within 2-fold, of a value. Where particular values are described in the application and claims, unless otherwise stated the term "about" means within an acceptable error range for the particular value. For example, when referring to a period of time, e.g., hours, the present values (±20%) are more applicable. Thus, 6 hours can be, e.g., 4.8 hours, 5.5 hours, 6.5 hours, 7.2 hours, as well as the usual 6 hours. Another example includes a period of time measured in days such that "about" a week can refer to 6 days or 7 days or 8 days or any time in between such as 6 days 12 hours.

All references noted in this application, both patent literature and/or non-patent literature are incorporated herein by reference in their entirety. References that are not specifically singled out as being incorporated herein by reference in their entirety are nonetheless incorporated herein by reference in their entirety.

I claim:

1. A homeopathic formulation for oral care comprising:
   (a) a tincture of *Arnica montana* with one or more dilution of 3×, 6×, and 18×;
   (b) a tincture of *Calendula officinalis* with a dilution of 3×;
   (c) a tincture of *Chamomilla* with a dilution of 5×;
   (d) a tincture of *Ignatia amara* with a dilution of 30×;
   (e) at least one of a tincture of *Echinacea purpurea* or a tincture of *Echinacea angustifolia* with a dilution of 3×;
   (f) a tincture of *Ruta graveolens* with a dilution of 12×; and
   (g) a tincture of Hepar sulphuris *calcaneum* with a dilution of 8×;
   combined in a mixture with a solvent or co-solvent and an amount of one or more preservatives; wherein said amount of the one or more preservatives is 0.01% to 95% of the total weight (wt %) of the formulation; and wherein each dilution is according to the decimal scale.

2. The homeopathic formulation for oral care of claim 1, further comprising at least one selected from the group consisting of: a tincture of *Plantago major*; a tincture of *Origanum vulgare* L; a tincture of *Thymus vulgaris* L; a tincture of *Lavandula angustifolia*; a tincture of *Lavandula officinalis*; a tincture of *Salvia officinalis*; a tincture of *Melissa officinalis*; a tincture of *Cuminum cyminum*; a tincture of *Petroselinum crispum*; a tincture of *Tagetes erecta*; a tincture of *Boswellia sacra*; a tincture of *Sambucus nigra*; a tincture of *Copaifera langsdorfii*; a tincture of *Curcuma longa*; a tincture of *Allium* sativu; a tincture of *Punica granatum*; a tincture of *Euterpe oleracea*; a tincture of *Sophora flavescens*; a tincture of *Rheum rhabarbarum*; a tincture of *Fagopyrum esculentum*; a tincture of *Camellia sinensis*; a tincture of *Coptis teeta*; a tincture of *Hydrastis canadensis*; a tincture of *Mahonia aquifolium*; a tincture of *Phellodendron amurense*; a tincture of *Berberis vulgaris*; a tincture of *Xanthorhiza simplicissima*; a tincture of *Lonicera* ceprifoliu; a tincture of *Vaccinium macrocarpon*; a tincture of *Cinnamomum zeylanicum* Nees; a tincture of *Cinnamomum verum*; a tincture of *Vitis vinifera*; a tincture of *Terminalia* bellerica; a tincture of *Pinus pinaster*; a tincture of *Albizia lebbek*; a tincture of *Melia azadirachta*; a tincture of *Salvadora persica*; a tincture of *Paullinia cupana*; a tincture of *Piper betle*; a tincture of *Syzygium aromaticum*; a tincture of *Commiphora myrrha*; a tincture of *Juglans regia*; a tincture of *Scutellaria baicalensis*; a tincture of *Magnolia officinalis*; a tincture of *Origanum onites*; a tincture of *Origanum majorana*; a tincture of *Origanum heracleoticum*;

a tincture of *Thymus citriodorus*; a tincture of *Thymus pulegioides*; a tincture of *Thymus x herba-barona*; a tincture of *Thymus serpyllum*; a tincture of *Lavandula stoechas*; a tincture of *Lavandula dentate*; a tincture of *Lavandula x intermedia*; a tincture of *Lavandula multifida*; a tincture of *Salvia divinorum*; a tincture of *Salvia apiana*; a tincture of *Calendula arvensis*; a tincture of *Calendula maderensis*; a tincture of *Tagetes minuta*; a tincture of *Tagetes patula*; a tincture of *Boswellia frereana*; a tincture of *Boswellia serrata*; a tincture of *Boswellia papyrifera*; a tincture of *Sambucus melanocarpa*; a tincture of *Sambucus racemosa*; a tincture of *Rheum rhaponticum*; a tincture of *Citrullus colocynthis*; and a tincture of *Cucumis sativus*.

3. The homeopathic formulation for oral care of claim 2, further comprising a tincture of *Gelsemium*.

4. The homeopathic formulation for oral care of claim 2, further comprising a tincture of *Aconitum napellus*.

5. The homeopathic formulation for oral care of claim 2, further comprising a tincture of *Hypericum*.

6. The homeopathic formulation for oral care of claim 2, further comprising a tincture of *Mercurius vivus*.

7. The homeopathic formulation for oral care of claim 2, further comprising at least one of an allopathic medicine, a vitamin, a mineral, an amino acid, and an inert substance.

8. The homeopathic formulation for oral care of claim 2, wherein the solvent or co-solvent is selected from the group consisting of: alcohol, water, water-alcohol mixture, glycerine, and isotonic sodium chloride solution.

9. The homeopathic formulation for oral care of claim 1, wherein the composition is a gel, a spray, or a rinse.

10. The homeopathic formulation for oral care of claim 9, further comprising a tincture of *Mercurius vivus* with a dilution of 10× according to the decimal scale.

11. The homeopathic formulation for oral care of claim 9, further comprising a tincture of *Hypericum* with a dilution of 10× according to the decimal scale.

12. The homeopathic formulation for oral care of claim 9, wherein the formulation is a gel, wherein the gel further comprises allantoin, hydroxyethyl cellulose, peppermint oil, purified water, sodium benzoate, and xylitol.

13. The homeopathic formulation for oral care of claim 9, wherein the formulation is drops or a spray, wherein the drops or spray further comprises citric acid, glycerin, potassium sorbate, and purified water.

14. A homeopathic formulation for oral care comprising:
(a) a tincture of *Arnica montana* in a dilution of 3×, 6×, or 18×,
(b) a tincture of *Calendula officinalis* with a dilution of 3×,
(c) a tincture of *Chamomilla* with a dilution of 5×,
(d) a tincture of *Ignatia amara* with a dilution of 30×,
(e) at least one of a tincture of *Echinacea purpurea* or a tincture of *Echinacea angustifolia* with a dilution of 3×,
(f) a tincture of *Ruta graveolens* with a dilution of 12×, and
(g) a tincture of Hepar sulphuris *calcaneum* with a dilution of 8×,
combined in a mixture with a solvent or co-solvent and an amount of one or more added preservatives selected from the group consisting of potassium sorbate and citric acid;
wherein said amount of the one or more preservatives is 0.01% to 95% of the total weight (wt %) of the formulation; and wherein each dilution is according to the decimal scale.

15. A homeopathic formulation for oral care comprising:
(a) a tincture of *Arnica montana* with one or more dilution of 3×, 6×, and 18×;
(b) a tincture of *Calendula officinalis* with a dilution of 3×;
(c) a tincture of *Chamomilla* with a dilution of 5×;
(d) a tincture of *Ignatia amara* with a dilution of 30×;
(e) at least one of a tincture of *Echinacea purpurea* or a tincture of *Echinacea angustifolia* with a dilution of 3×;
(f) a tincture of *Ruta graveolens* with a dilution of 12×; and
(g) a tincture of Hepar sulphuris *calcareum* with a dilution of 8×;
combined in a mixture with a solvent or co-solvent an amount of potassium sorbate and citric acid; wherein said amount of potassium sorbate and citric is 0.01% to 95% of the total weight (wt %) of the formulation; and wherein each dilution is according to the decimal scale.

16. A homeopathic formulation for oral care comprising:
(a) a tincture of *Arnica montana* with one or more dilution of 3×, 6×, and 18×;
(b) a tincture of *Calendula officinalis* with a dilution of 3×;
(c) a tincture of *Chamomilla* with a dilution of 5×;
(d) a tincture of *Ignatia amara* with a dilution of 30×;
(e) at least one of a tincture of *Echinacea purpurea* or a tincture of *Echinacea angustifolia* with a dilution of 3×;
(f) a tincture of *Ruta graveolens* with a dilution of 12×; and
(g) a tincture of Hepar sulphuris *calcareum* with a dilution of 8×;
combined in a mixture with a solvent or co-solvent and an amount of sodium benzoate;
wherein said amount of sodium benzoate is 0.01% to 95% of the total weight (wt %) of the formulation; and wherein each dilution is according to the decimal scale.

17. A homeopathic formulation for oral care comprising:
(a) a tincture of *Arnica montana* with one or more dilution of 3×, 6×, and 18×;
(b) a tincture of *Calendula officinalis* with a dilution of 3×;
(c) a tincture of *Chamomilla* with a dilution of 5×;
(d) a tincture of *Ignatia amara* with a dilution of 30×;
(e) at least one of a tincture of *Echinacea purpurea* or a tincture of *Echinacea angustifolia* with a dilution of 3×;
(f) a tincture of *Ruta graveolens* with a dilution of 12×; and
(g) a tincture of Hepar sulphuris *calcareum* with a dilution of 8×;
combined in a mixture with a solvent or co-solvent and an amount of potassium sorbate;
wherein said amount of potassium sorbate is 0.01% to 95% of the total weight (wt %) of the formulation; and wherein each dilution is according to the decimal scale.

\* \* \* \* \*